US011351325B2

(12) United States Patent
Martin et al.

(10) Patent No.: US 11,351,325 B2
(45) Date of Patent: Jun. 7, 2022

(54) DUAL-CONNECTOR WYE PIECE

(71) Applicant: Fisher & Paykel Healthcare Limited, Auckland (NZ)

(72) Inventors: Madeleine Bess Martin, Auckland (NZ); David Robert Kemps, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 287 days.

(21) Appl. No.: 16/178,485

(22) Filed: Nov. 1, 2018

(65) Prior Publication Data

US 2019/0111229 A1 Apr. 18, 2019

Related U.S. Application Data

(63) Continuation of application No. 14/762,755, filed as application No. PCT/NZ2014/000007 on Jan. 21, 2014, now Pat. No. 10,143,818.

(60) Provisional application No. 61/755,300, filed on Jan. 22, 2013.

(51) Int. Cl.
*A61M 16/08* (2006.01)
*A61M 16/12* (2006.01)
*A61M 16/00* (2006.01)

(52) U.S. Cl.
CPC .... *A61M 16/0833* (2014.02); *A61M 16/0841* (2014.02); *A61M 16/0858* (2014.02); *A61M 16/12* (2013.01); *A61M 2016/0027* (2013.01)

(58) Field of Classification Search
CPC .............. A61M 16/08; A61M 16/0816; A61M 16/0833; A61M 16/0841; A61M 16/085; A61M 16/0858; A61M 16/12; A61M 2016/0027; F16L 41/021; F16L 41/023
See application file for complete search history.

(56) References Cited

U.S. PATENT DOCUMENTS 3,903,884 A 9/1975 Huston et al.
4,020,834 A 5/1977 Bird
(Continued)

FOREIGN PATENT DOCUMENTS

AU 2009245802 B2 11/2013
AU 2015264908 A1 12/2015
(Continued)

OTHER PUBLICATIONS

International Preliminary Report on Patentability in corresponding International Patent Application No. PCT/NZ2014/000007, dated Aug. 6, 2015, in 7 pages.
(Continued)

*Primary Examiner* — Joseph D. Boecker
(74) *Attorney, Agent, or Firm* — Knobbe Martens Olson & Bear, LLP

(57) ABSTRACT

A wye connector has a patient coupling end. The patient coupling end has a first connector surface and a second connector surface. The first connector surface has a first diameter at an axial location along the patient coupling end. The second connector surface has a second diameter at the same axial location along the patient coupling end. The first diameter is larger than the second diameter. The second connector surface projects axially outward beyond the first connector surface.

24 Claims, 12 Drawing Sheets

(56) References Cited

U.S. PATENT DOCUMENTS

| | | | |
|---|---|---|---|
| 4,248,217 A * | 2/1981 | Brisson | A61M 16/1075 128/203.27 |
| 4,333,451 A * | 6/1982 | Paluch | A61M 16/0808 128/205.12 |
| 4,557,261 A | 12/1985 | Rugheimer | |
| 4,558,708 A * | 12/1985 | Labuda | A61M 16/08 128/207.14 |
| 4,668,218 A | 5/1987 | Virtanen | |
| 4,723,543 A | 2/1988 | Beran | |
| 4,773,448 A | 9/1988 | Francis | |
| 4,787,655 A | 11/1988 | Gross et al. | |
| 4,817,822 A | 4/1989 | Rand et al. | |
| 4,819,629 A | 4/1989 | Jonson | |
| 5,036,840 A | 8/1991 | Wallace | |
| 5,062,420 A * | 11/1991 | Levine | A61M 16/0833 128/204.18 |
| 5,178,138 A | 1/1993 | Walstrom et al. | |
| 5,195,980 A | 3/1993 | Catlin | |
| 5,228,436 A | 3/1993 | Parkin | |
| 5,297,543 A | 3/1994 | Larson et al. | |
| D362,503 S | 9/1995 | Cook et al. | |
| 5,460,172 A * | 10/1995 | Eckerbom | A61M 16/1045 128/201.13 |
| 5,546,930 A | 8/1996 | Wikefeldt | |
| 5,735,271 A * | 4/1998 | Lorenzen | A61M 16/0463 128/200.26 |
| 5,776,117 A | 7/1998 | Haselhorst et al. | |
| 5,988,164 A | 11/1999 | Paluch | |
| 6,102,038 A * | 8/2000 | DeVries | A61M 16/208 128/204.23 |
| 6,209,539 B1 * | 4/2001 | Loescher | A61M 16/08 128/204.17 |
| D492,030 S | 6/2004 | Rani | |
| D492,773 S | 7/2004 | Elllingboe et al. | |
| D519,632 S | 4/2006 | Bayron et al. | |
| 7,152,597 B2 | 12/2006 | Bathe | |
| 7,162,921 B2 | 1/2007 | Gerder et al. | |
| D547,447 S | 7/2007 | Bruce et al. | |
| 7,634,998 B1 | 12/2009 | Fenley | |
| 7,841,341 B2 | 11/2010 | Dhuper et al. | |
| 7,926,484 B2 | 4/2011 | Dhuper et al. | |
| D649,240 S | 11/2011 | Lewis et al. | |
| 8,151,794 B2 | 4/2012 | Meyer et al. | |
| D672,459 S | 12/2012 | Miller | |
| D685,906 S | 7/2013 | Dale et al. | |
| D689,187 S | 9/2013 | Kruger | |
| D691,717 S | 10/2013 | McLean et al. | |
| 8,746,241 B2 | 6/2014 | Cavendish | |
| D709,612 S | 7/2014 | Lewis | |
| D723,681 S | 3/2015 | Ingram et al. | |
| 10,143,818 B2 | 12/2018 | Martin et al. | |
| 2005/0188990 A1 | 9/2005 | Fukunaga et al. | |
| 2005/0229928 A1 | 10/2005 | Irvi et al. | |
| 2006/0173420 A1 | 8/2006 | Fangrow, Jr. | |
| 2006/0283447 A1 | 12/2006 | Dhuper et al. | |
| 2007/0193581 A1 | 8/2007 | Laurila et al. | |
| 2008/0077063 A1 | 3/2008 | Meyer et al. | |
| 2008/0264412 A1 * | 10/2008 | Meyer | A61M 15/009 128/200.22 |
| 2008/0264418 A1 | 10/2008 | Schermeier et al. | |
| 2009/0105692 A1 | 4/2009 | Lopez et al. | |
| 2009/0124983 A1 | 5/2009 | Ferrari | |
| 2009/0301476 A1 | 12/2009 | Korneff et al. | |
| 2010/0071688 A1 * | 3/2010 | Dwyer | A61M 15/0025 128/200.18 |
| 2010/0071695 A1 * | 3/2010 | Thiessen | A61M 16/0833 128/204.18 |
| 2010/0139653 A1 | 6/2010 | Schloss | |
| 2010/0163022 A1 | 7/2010 | Brewer et al. | |
| 2010/0163051 A1 | 7/2010 | Brewer et al. | |
| 2011/0088696 A1 | 4/2011 | Ratner | |
| 2011/0146670 A1 * | 6/2011 | Gallem | A61M 16/0833 128/200.14 |
| 2011/0284007 A1 * | 11/2011 | Pierre | A61M 16/1045 128/201.13 |
| 2012/0180791 A1 | 7/2012 | Ciccone et al. | |
| 2012/0255545 A1 | 10/2012 | Meyer et al. | |
| 2013/0269686 A1 | 10/2013 | Pezzano et al. | |
| 2014/0276178 A1 | 9/2014 | Simon | |
| 2015/0021909 A1 | 1/2015 | Gulliver et al. | |
| 2015/0314093 A1 | 11/2015 | Chiu | |
| 2016/0038700 A1 | 2/2016 | White et al. | |
| 2017/0246417 A1 | 8/2017 | Kemps et al. | |
| 2020/0289780 A1 | 9/2020 | Kemps et al. | |

FOREIGN PATENT DOCUMENTS

| | | | | |
|---|---|---|---|---|
| CN | 201912587 U | 8/2011 | | |
| DE | 3703441 A1 | 8/1988 | | |
| DE | 102007009449 B3 | 1/2008 | | |
| DE | 202011107902 U1 | 1/2012 | | |
| EP | 0604399 A1 * | 6/1994 | | A61M 16/08 |
| EP | 0604399 A1 | 6/1994 | | |
| EP | 1820528 A1 | 8/2007 | | |
| EP | 2044921 B1 | 7/2011 | | |
| FR | 2725627 | 10/1994 | | |
| GB | 750672 A | 6/1956 | | |
| GB | 1290484 A | 9/1972 | | |
| GB | 1317315 A | 5/1973 | | |
| GB | 2412877 A | 10/2005 | | |
| JP | 2004-033550 A | 2/2004 | | |
| WO | WO 1999/059517 A1 | 11/1999 | | |
| WO | WO 2003/041780 A2 | 5/2003 | | |
| WO | WO 2005/048982 | 6/2005 | | |
| WO | WO-2012030232 A1 * | 3/2012 | | A61M 16/00 |
| WO | WO 2013/147623 A1 | 10/2013 | | |
| WO | WO 2013/162386 A1 | 10/2013 | | |
| WO | WO 2014/116122 | 7/2014 | | |
| WO | WO 2015/174859 A2 | 11/2015 | | |

OTHER PUBLICATIONS

International Search Report for PCT/NZ2014/000007 dated Jun. 26, 2014 in 3 pages.

* cited by examiner

DUAL-CONNECTOR WYE PIECE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. application Ser. No. 14/762,755, filed Jul. 22, 2015, which is a national phase of International Application No. PCT/NZ2014/000007, filed Jan. 21, 2014, which claims the priority benefit of U.S. Provisional Patent Application No. 61/755,300, filed on Jan. 22, 2013, which is hereby incorporated by reference in its entirety.

BACKGROUND OF THE INVENTION

Field of the Invention

The present invention generally relates to a patient wye for use in connecting medical respiration or ventilation systems. More particularly, the present invention relates to a patient wye in which the patient end is configured for separate mating with two different components.

Description of the Related Art

A ventilator is a machine designed to mechanically move breathable air into and out of the lungs. The ventilator provides the mechanism of breathing for a patient who is physically unable to breathe or who is breathing insufficiently.

A breathing circuit connects the ventilator to a patient interface, such as an endotracheal tube or a mask, for example but without limitation. The breathing circuit can include an inspiratory conduit and an expiratory conduit. The inspiratory conduit delivers breathing gases while the expiratory conduit returns gases to the ventilator.

SUMMARY OF THE INVENTION

A wye connects the inspiratory conduit and the expiratory conduit to a patient outlet, which can be joined to a patient interface (possibly through an additional short conduit). In some configurations, the wye includes a standard 22 mm taper male connector to couple the patient outlet of the wye to mask-style interfaces. In some configurations, the wye includes a standard 15 mm taper female connector to couple the patient outlet of the wye to endotracheal tube-style interfaces. In some configurations, the wye includes both the standard 15 mm taper female connector and the standard 22 mm taper male connector.

Applicant has found, however, that wyes with both connectors generally have both connectors (i.e., the 15 mm female and the 22 mm male) terminating at the same axial location. Thus, such wyes result in the female connector being shrouded by the male connector. With a shrouded female connector, the medical professional making connections may become confused regarding how to make the connections with the 15 mm male connector at the end of the endotracheal component. Accordingly, one aspect of the present invention relates to the recognition that having an enshrouded female connector that does not protrude beyond the male connector can cause issues with making a proper connection of components.

It is therefore an object of certain features, aspects and advantages of the present invention to provide a wye connector that overcomes or at least ameliorates one or more of the disadvantages of the prior art, or alternatively at least provides the public or industry with a useful choice.

Further objects of the invention may become apparent from the following description.

Accordingly, a wye connector that is arranged and configured in accordance with certain features, aspects and advantages of the present invention can include a body with a patient end, an inspiratory end and an expiratory end in which the patient end includes a male connector that encircles a female connector and in which the female connector protrudes beyond the male connector.

In some configurations, a wye connector comprises a patient coupling end. The patient coupling end has a first connector surface and a second connector surface. The first connector surface has a first diameter at an axial location along the patient coupling end. The second connector surface has a second diameter at the same axial location along the patient coupling end. The first diameter is larger than the second diameter. At least a portion of the second connector surface projects axially outward beyond the first connector surface.

In some such configurations, the first connector surface is formed on a first connector portion and the second connector surface is formed on a second connector portion with the first connector portion and the second connector portion being separated by a gap.

In some such configurations, the first connector surface terminates proximally of the gap.

In some such configurations, the gap is isolated from flow through the patient coupling end of the wye connector.

In some such configurations, the first connector surface comprises a male taper connector and the second connector surface comprises a female taper connector.

In some such configurations, the male taper connector is a 22 mm male taper connector and the female taper connector is a 15 mm female taper connector.

In some configurations, the wye connector further comprises an inspiratory connector end and an expiratory connector end with the inspiratory connector end defining at least a portion of an inspiratory branch and the expiratory connector end defining at least a portion of an expiratory branch.

In some such configurations, the inspiratory connector end defines an inspiratory flow lumen having an inspiratory flow lumen axis and the expiratory connector end defines an expiratory flow lumen having an expiratory flow lumen axis with the inspiratory flow lumen axis and the expiratory flow lumen axis extending generally parallel to each other.

In some such configurations, the wye connector further comprises a probe port positioned between the inspiratory connector end and the patient coupling end.

In some such configurations, the probe port is positioned along the inspiratory branch.

In some configurations, the wye connector further comprises an introduction port positioned between the inspiratory connector end and the patient coupling end.

In some such configurations, the introduction port is positioned between the inspiratory branch and the expiratory branch.

BRIEF DESCRIPTION OF THE DRAWINGS

These and other features, aspects and advantages of the present invention will be described with reference to the following drawings.

DETAILED DESCRIPTION OF THE PREFERRED EMBODIMENT

Figure 1:
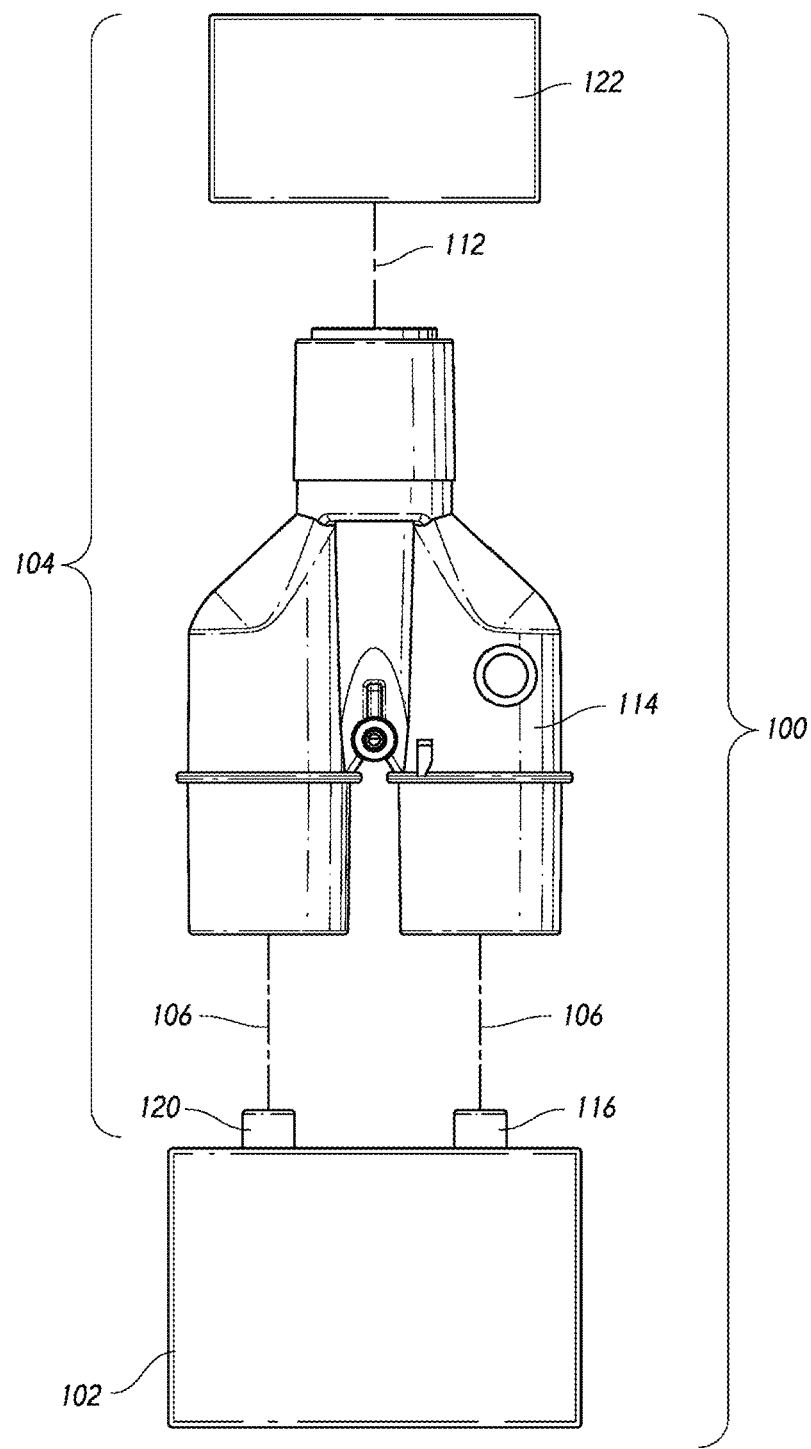
FIG. 1 is a schematic representation of a mechanical ventilation system that can be used with a wye connector that is arranged and configured in accordance with certain features, aspects and advantages of the present invention.

With reference initially to FIG. 1, a mechanical ventilation system 100 is schematically illustrated. In general, the system 100 comprises a ventilator 102 connected to a patient circuit 104.

The patient circuit 104 can comprise an inspiratory limb 106, an expiratory limb 110 and a patient limb 112. The inspiratory limb 106, the expiratory limb 110 and the patient limb 112 can be connected to one another by a patient wye 114. The inspiratory limb 106 and the expiratory limb 110 respectively connect the patient wye 114 to a supply port 116 and a return port 120 of the ventilator 102 in the illustrated configuration.

The patient limb 112 connects the patient wye 114 to a patient interface 122. In some configurations, the patient interface 122 can be used for invasive ventilation and, in such configurations, the patient wye 114 can be configured to connect to a tracheotomy tube or an endotracheal tube, for example. In some configurations, the patient interface 122 can be used for noninvasive ventilation and, in such configurations, the patient can include a breathing mask, such as a nasal mask, an oral mask, an oral-nasal mask, a nasal cannula or the like. As will be described, the patient wye 114 can be configured to include a plurality of connectors used to connect to different interfaces 122.

The ventilator 102 generally operates to provide a supply of breathing gas to the inspiratory limb 106 for delivery to the patient interface 122 via the patient wye 114 and the patient limb 112. The ventilator 102 may receive exhaled air from the patient that is delivered to an exhalation valve or similar device on the ventilator. The exhaled air may pass from the patient interface 122, through the patient limb 112, through the patient wye 114 and through the expiratory limb 110.

Figure 2:
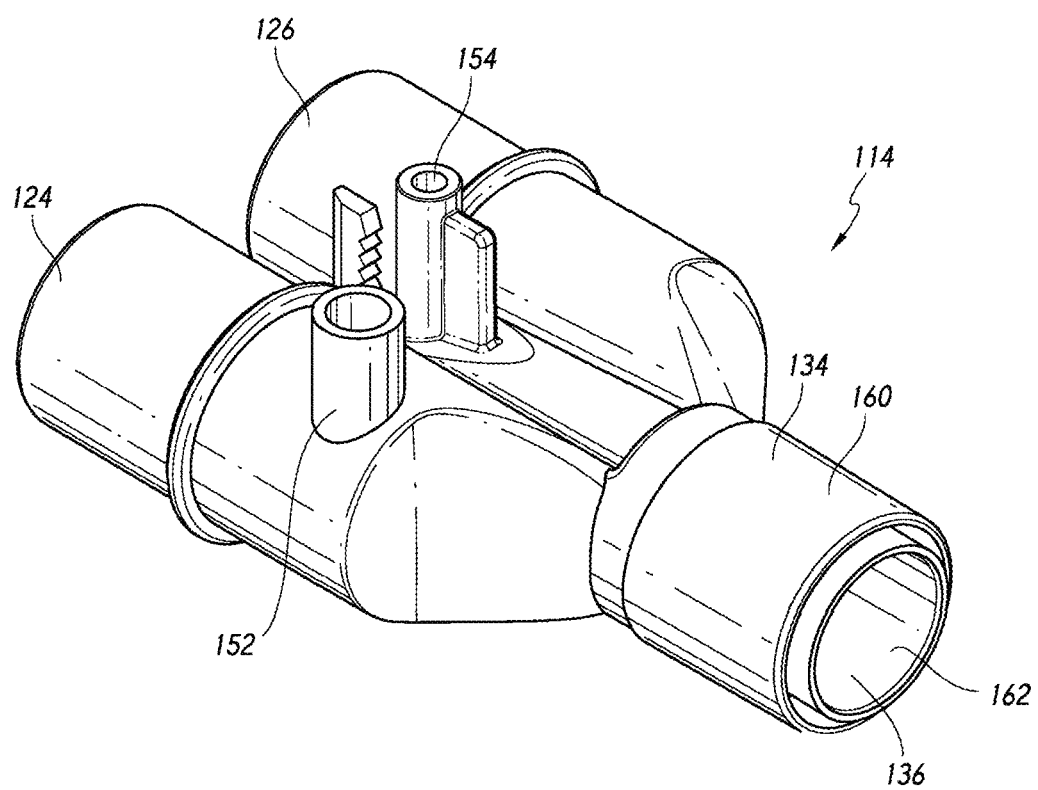
FIG. 2 is a perspective view of a wye connector that is arranged and configured m accordance with certain features, aspects and advantages of the present invention.
Figure 3:
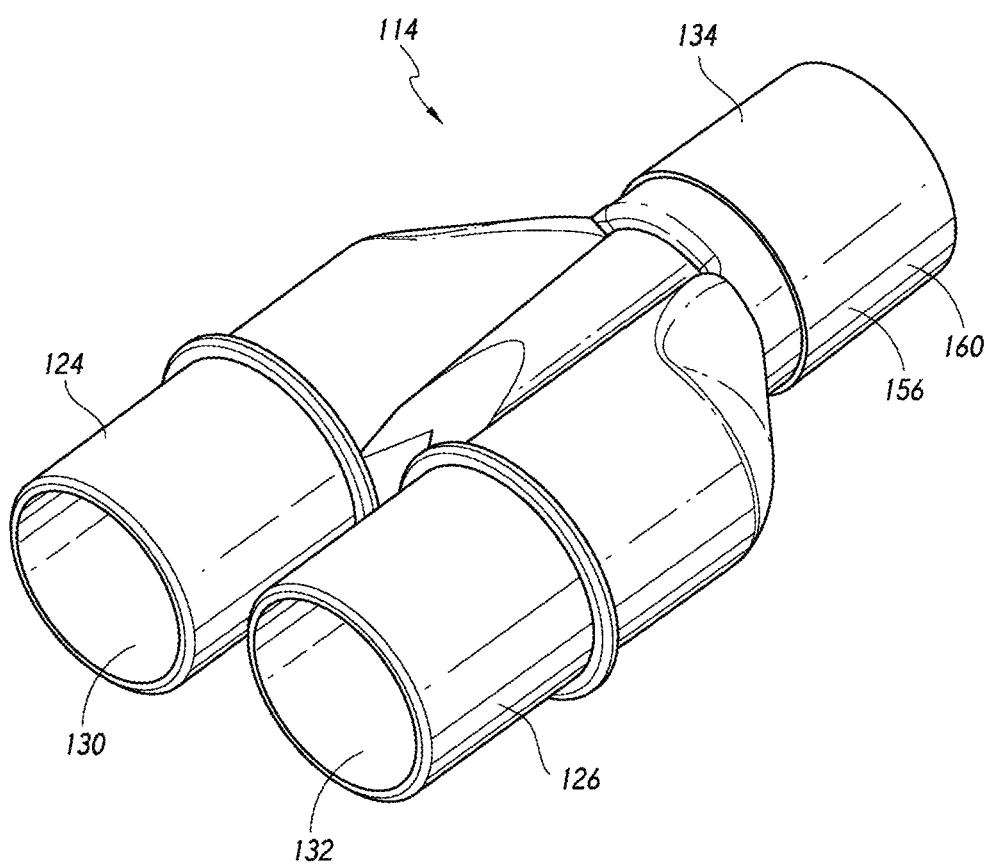
FIG. 3 is another perspective view of the wye connector of FIG. 2.
Figure 4:
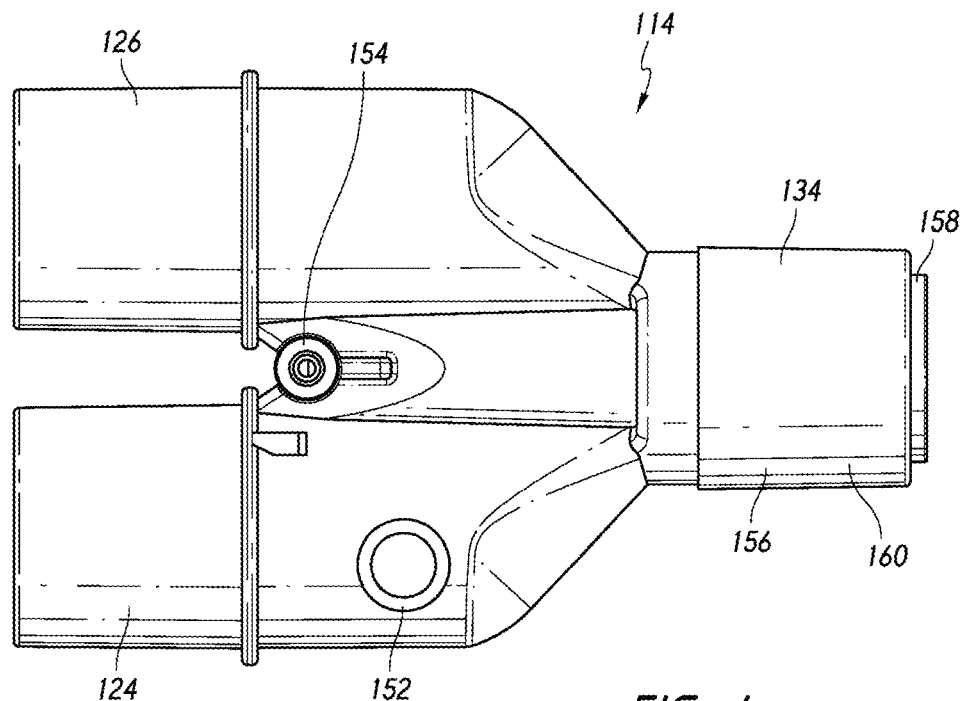
FIG. 4 is a top view of the wye connector of FIG. 2.
Figure 5:
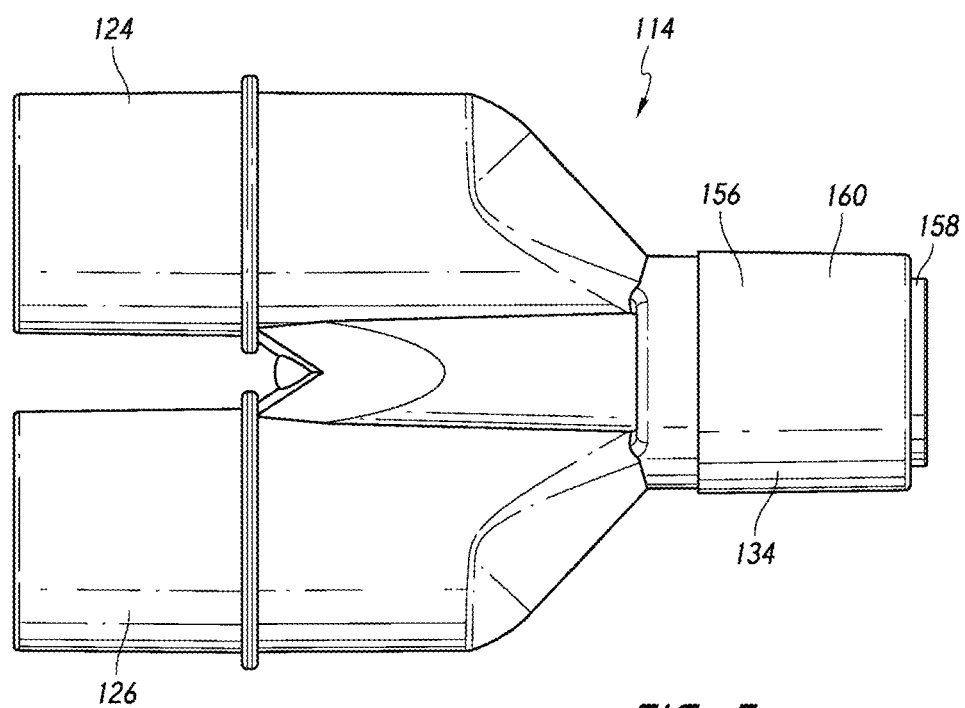
FIG. 5 is a bottom view of the wye connector of FIG. 2.
Figure 6:
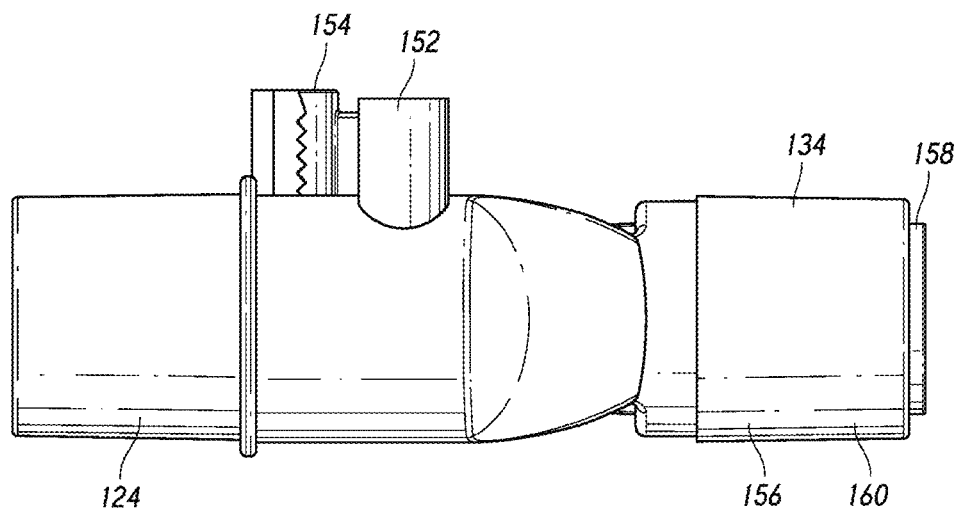
FIG. 6 is a left side view of the wye connector of FIG. 2.
Figure 7:
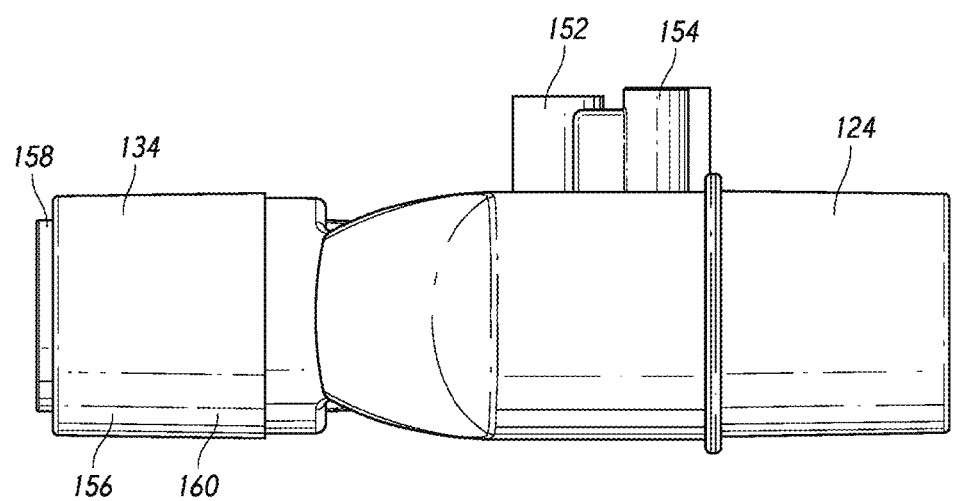
FIG. 7 is a right side view of the wye connector of FIG. 2.
Figure 8:
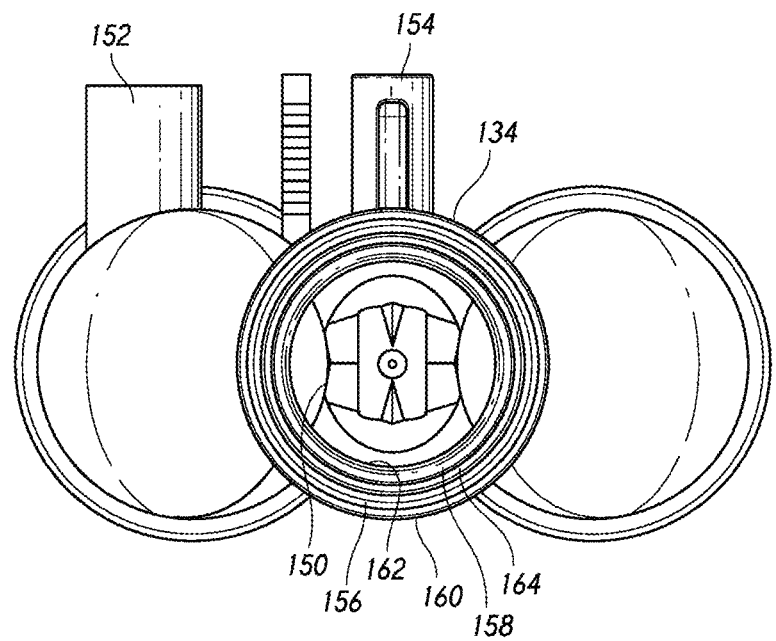
FIG. 8 is a front view of the wye connector of FIG. 2.
Figure 9:
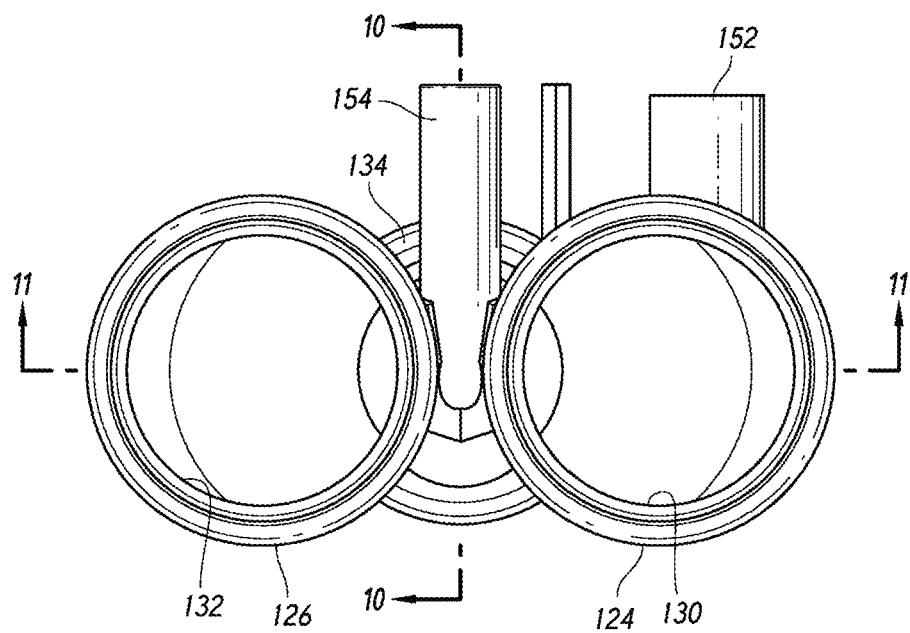
FIG. 9 is a rear view of the wye connector of FIG. 2.
Figure 12:
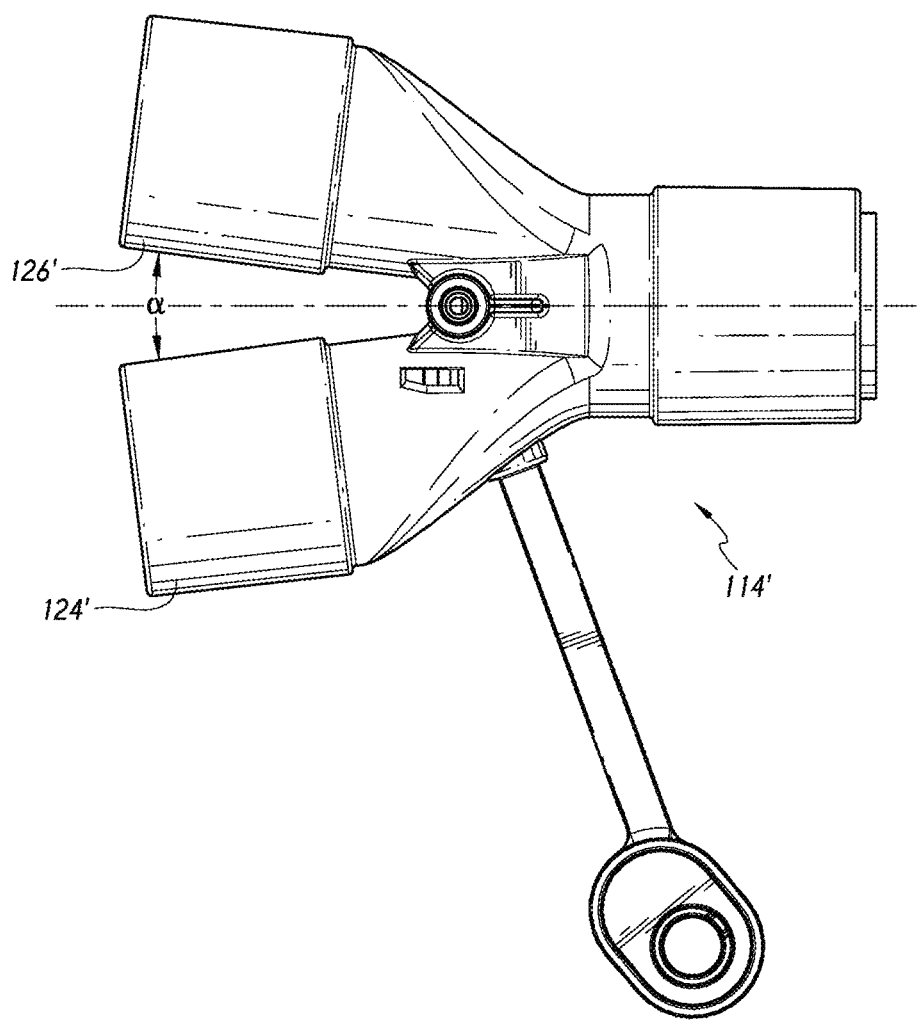
FIG. 12 is a top view of another wye connector that is arranged and configured m accordance with certain features, aspects and advantages of the present invention.
Figure 13:
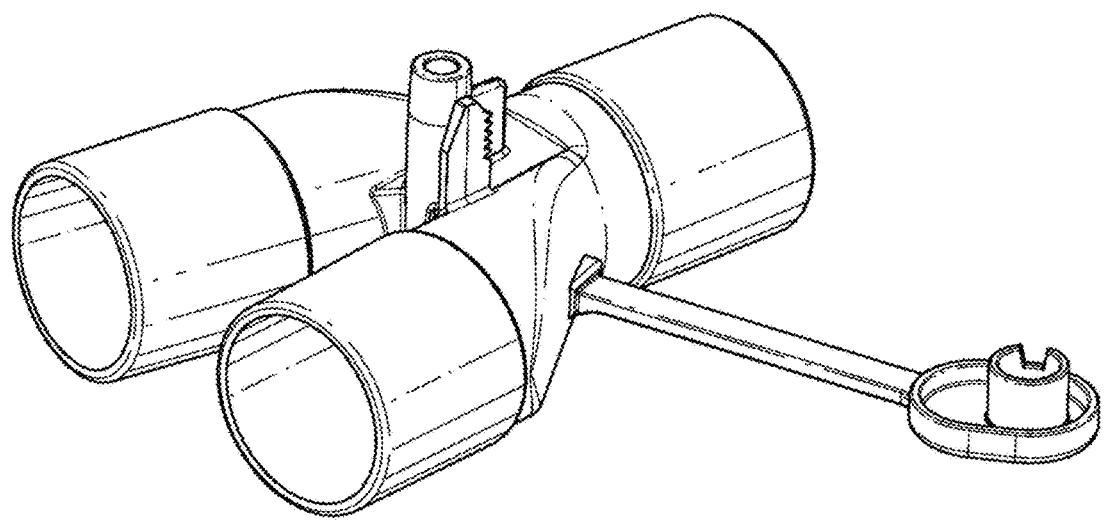
FIG. 13 is a perspective view of the wye connector of FIG. 12.
Figure 14:
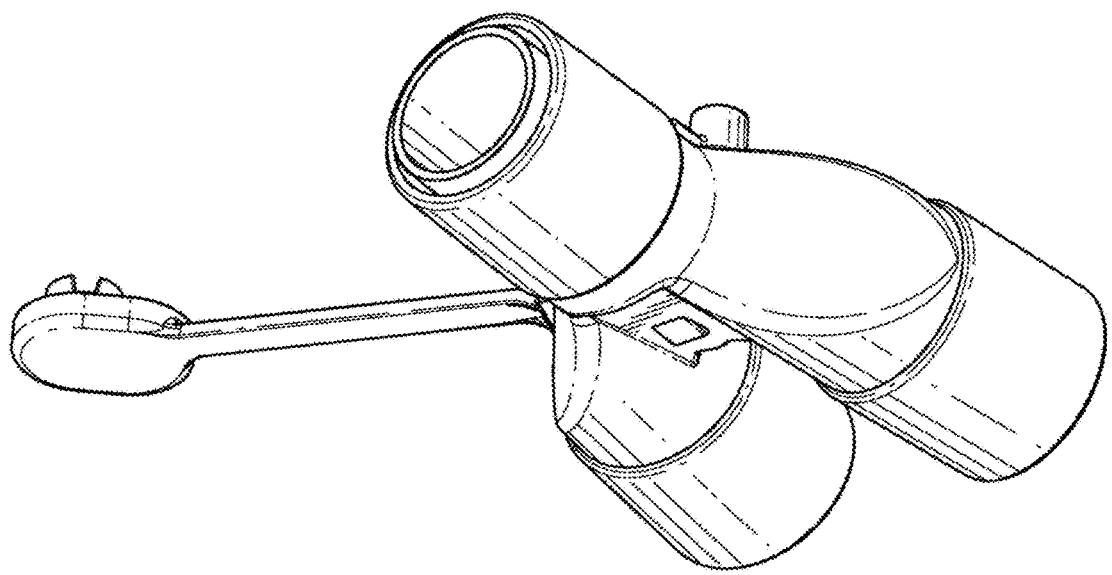
FIG. 14 is another perspective view of the wye connector of FIG. 12.
Figure 15:
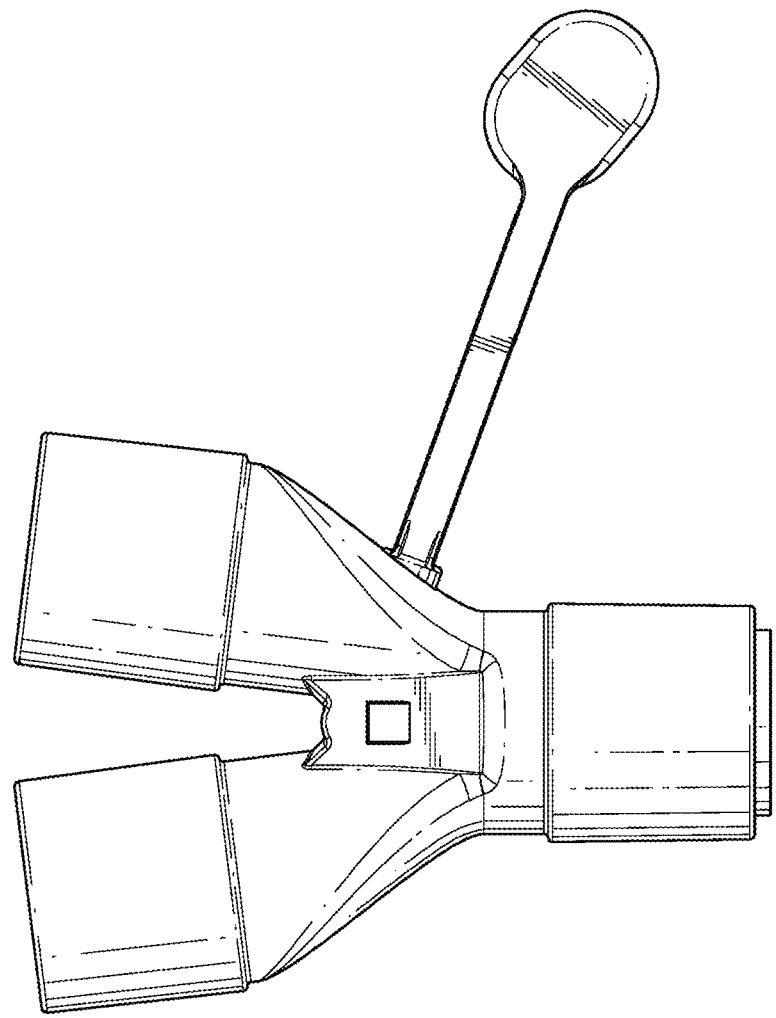
FIG. 15 is a bottom view of the wye connector of FIG. 12.
Figure 16:
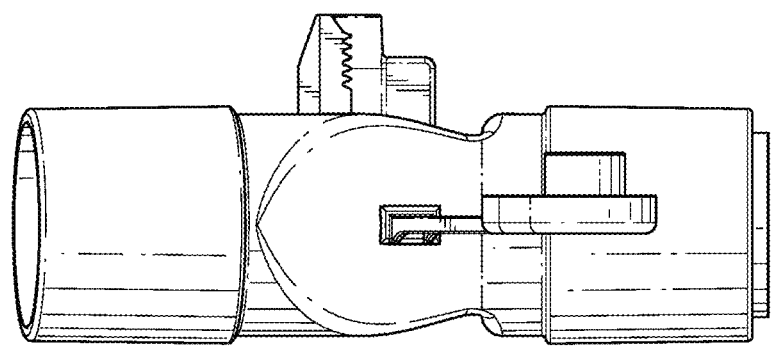
FIG. 16 is a first side view of the wye connector of FIG. 12.
Figure 17:
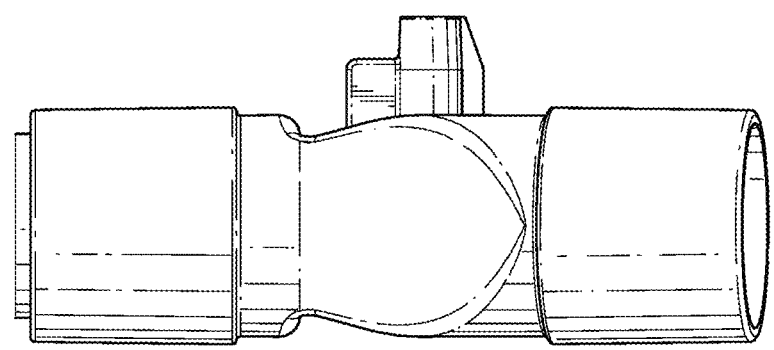
FIG. 17 is a second side view of the wye connector of FIG. 12.
Figure 18:
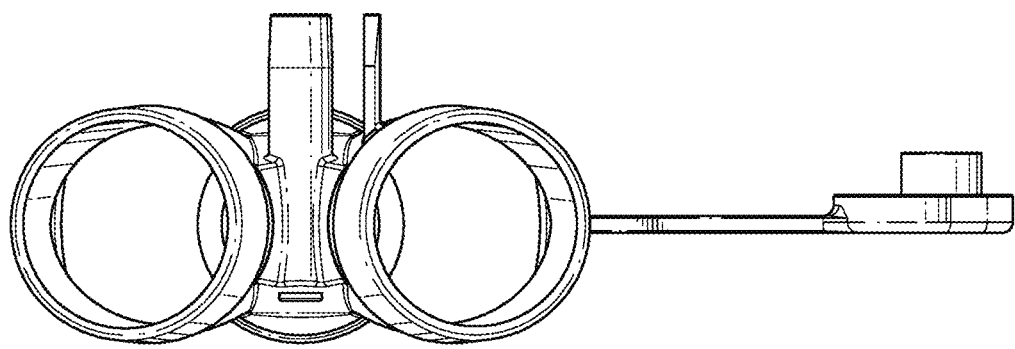
FIG. 18 is a first end view of the wye connector of FIG. 12.
Figure 19:
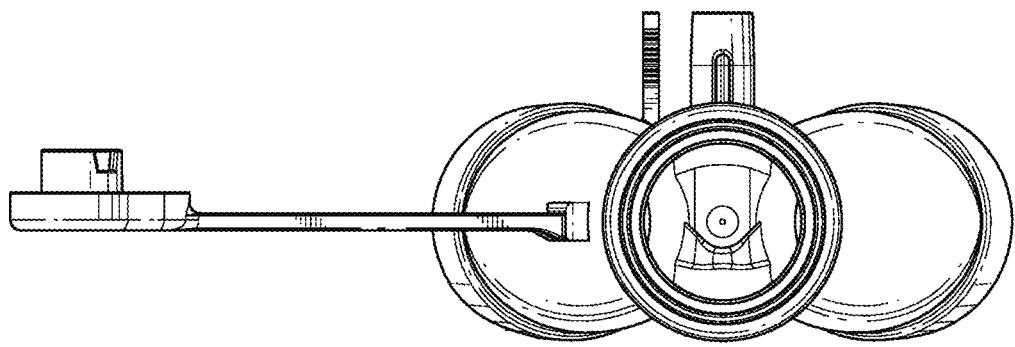
FIG. 19 is a second end view of the wye connector of FIG. 12.

With reference now to FIG. 2, the patient wye 114 will be described in greater detail. In general, the patient wye 114 is an open, three-flow passage connector. The patient wye 114 places the patient limb 112 of the patient circuit 104 in communication with the inspiratory limb 106 and the expiratory limb 110. As such, the patient wye comprises an inspiratory coupling end 124 and an expiratory coupling end 126. In the configuration of FIG. 2, the inspiratory coupling end 124 and the expiratory coupling end 126 are formed in members that extend generally parallel to each other (see FIG. 4). Other configurations are possible. In other words, the inspiratory connector end 124 can define an inspiratory flow lumen having an inspiratory flow lumen axis and the expiratory connector end 126 can define an expiratory flow lumen having an expiratory flow lumen axis. The inspiratory flow lumen axis and the expiratory flow lumen axis can extend generally parallel to each other. For example, in the configuration of FIG. 12, the illustrated patient wye 114' comprises an inspiratory coupling end 124' and an expiratory coupling end 126' that diverge from each other. The two ends 124' and 126' can diverge by an angle a. In some configurations, the angle a can be as small as about 2° and as large as about 30° but any suitable angle a can be used. By diverging instead of being parallel, connections are more easily made with the conduits.

An inspiratory opening 130 can be positioned on the inspiratory coupling end 124 and an expiratory opening 132 can be positioned on the expiratory coupling end 124. In the illustrated configuration, the inspiratory opening 130 is disposed at the end of the inspiratory coupling end 124. In the illustrated configuration, the inspiratory opening 130 is centered on a flow axis of the inspiratory coupling end 124. In the illustrated configuration, the expiratory opening 132 is disposed at the end of the expiratory coupling end 126. In the illustrated configuration, the expiratory opening 132 is centered on a flow axis of the expiratory coupling end 126.

The inspiratory coupling end 124 can include an inspiratory limb connection surface to which an end of the inspiratory limb can connect. Similarly, the expiratory coupling end 126 can include an expiratory limb connection surface to which an end of the expiratory limb can connect. In some configurations, the connection between the inspiratory limb 106 and the inspiratory coupling end 124 and/or the connection between the expiratory limb 110 and the expiratory coupling end 126 can be established by a pressure or friction fitting. Any other suitable type of fitting also can be used.

The patient wye 114 also comprises a patient coupling end 134. A patient opening 136 can be positioned on the patient coupling end 134.

Figure 11:
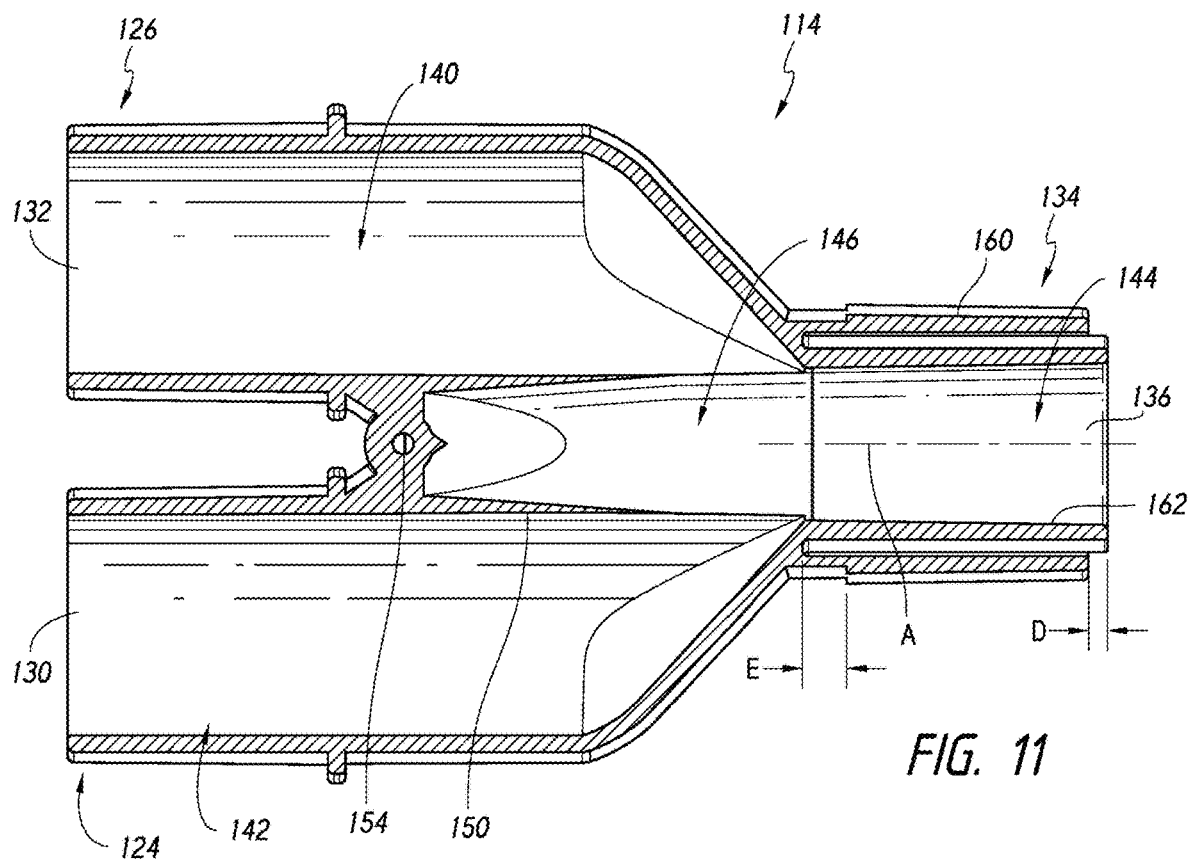
FIG. 11 is a section view of the wye connector of FIG. 2 taken along the line 11-11 in FIG. 9.

As shown in FIG. 11, within the patient wye 114, an inspiratory branch 140, an expiratory branch 142 and a patient branch 144 can be defined. The inspiratory branch 140 and the expiratory branch 142 join with the patient branch 144 in a merge region 146. The merge region 146 can include a portion that is separated from the inspiratory branch 140 and the expiratory branch 142 by a tapering wall 150.

One or more ports can be provided on the patient wye 114. For example, a probe port 152 and an introduction port 154 can be provided. The probe port 152 can be provided such that the probe port 152 intersects with the inspiratory branch 140 while the introduction port 154 can be positioned between the inspiratory branch 140 and the expiratory branch 142 within the portion of the merge region 146 that is substantially surrounded by the wall 150, for example. Other configurations also are possible. The probe port can be positioned between the inspiratory connector end and the patient coupling end. In some configurations, the probe port is positioned along the inspiratory branch. The introduction port can be positioned between the inspiratory connector end and the patient coupling end. In some configurations, the introduction port can be positioned between the inspiratory branch and the expiratory branch.

Figure 10:
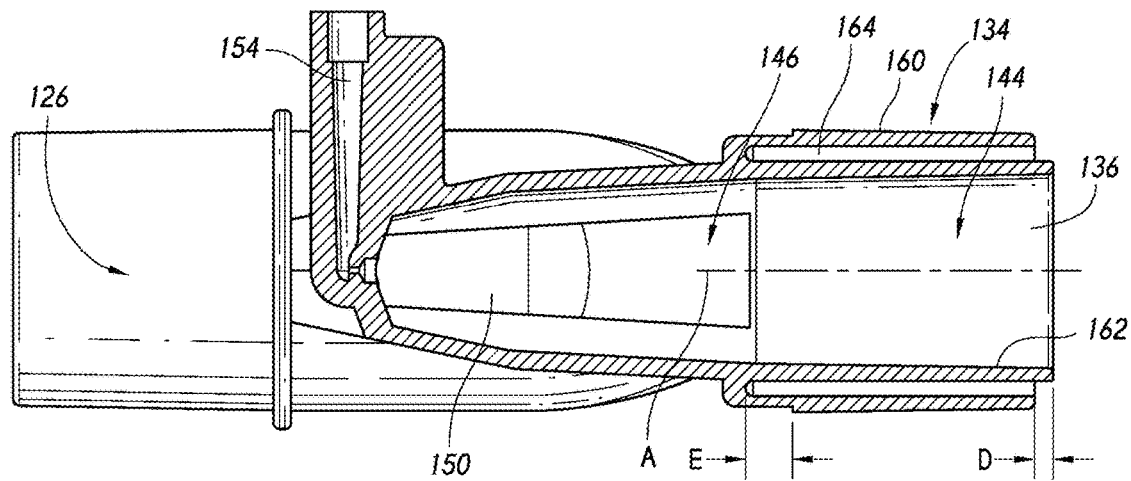
FIG. 10 is a section view of the wye connector of FIG. 2 taken along the line 10-10 in FIG. 9.

With reference now to FIGS. 10 and 11, the patient coupling end 134 will be described in more detail. The patient coupling end 134 comprises a first connector portion 156 that includes a first connector surface 160 and a second connector portion 158 that includes a second connector surface 162. In some configurations, the patient coupling end 134 merely comprises a first connector surface 160 and a second connector surface 162 that are formed on the same connector portion (e.g., inner and outer surfaces).

The first connector surface 160 can be formed as a portion of a male connector while the second connector surface 162 can be formed as a portion of a female connector. In the illustrated configuration, the first connector surface 160 extends around the second connector surface 162. In the illustrated configuration, the first connector surface 160 defines a male taper connector while the second connector surface 162 defines a female taper connector. In some configurations, the first connector surface 160 defines a 22 mm male taper connector while the second connector surface 162 defines a 15 mm female taper connector. In the illustrated configuration, the first connector surface 160 and the second connector surface 162 are symmetrically disposed about an axis A. In some such configurations, the first connector surface 160 has a first diameter at an axial location along the patient coupling end 134 and the second connector surface 162 has a second diameter at the same axial location along the patient coupling end 134 with the first diameter being larger than the second diameter.

With continued reference to FIGS. 10 and 11, a gap 164 can be defined between the first connector portion 156 and the second connector portion 158. The illustrated gap 164 is isolated from any flow within the wye 114. In some configurations, one or more airflow path can be provided in a proximal portion of the second connector portion, which path would be covered by a male connector that joins with the second connector surface and, therefore, would not cause system leaks during use.

In some configurations, all or at least a part of the gap can be solid or contain ribs. In some such configurations, the ribs can be axial ribs, radial ribs or ribs having other configurations. Advantageously, however, the gap 164 is generally void. The gap 164 allows movement or flexing of the two surfaces 160, 162 relative to each other. While movement relative to each other is less important (because both surfaces are not likely to be used at the same time), the ability of each surface to accommodate some relative movement is desirable. The gap 164, therefore, improves the flexibility of the connector surfaces 160, 162 while facilitating the large difference in diameters between the two connector surfaces 160, 162.

In some configurations, the outer first connector surface 160 terminates proximally of a distal-most end of the gap 164. In the illustrated configuration, the outer connector surface 160 terminates proximally of the gap 164. In the illustrated configuration, a distance E can be defined between the distal-most end of the gap 164 and the distal-most end of the outer connector surface 160. In some configurations, the distance E can be between about 0.5 mm and about 15 mm. Preferably, the distance E can be between about 1 mm and about 5 mm. More preferably, the distance E is about 3.6 mm. Other configurations are possible.

In some configurations, the second connector surface 162 terminates proximally of the first connector surface 160. In other words, the inner connector surface 162 projects in an axial direction proximally outward beyond the outer connector surface 160. While, in the illustrated configuration, the entire second connector portion 158 extends proximally beyond the first connector portion 156, in some configurations, only a portion of the second connector portion 158 may extend beyond the first connector portion 156. By projecting beyond the first connector portion 156, the projecting portion can attract attention to the existence of the second connector portion 158. In some configurations, at least a portion of the second connector portion 158 can project proximally of the first connector portion 156 by a distance D. The distance D can be between about 0.1 mm and about 8 mm. Preferably, the distance D can be between about 0.1 mm and about 2 mm. More preferably, the distance D is about 1.8 mm. In one configuration, the distance D is about 0.13 mm (about 5 mils).

Unless the context clearly requires otherwise, throughout the description, the words "comprise", "comprising", and the like, are to be construed in an inclusive sense as opposed to an exclusive or exhaustive sense, that is to say, in the sense of "including, but not limited to."

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the

What is claimed is:

1. A single piece wye connector comprising:
 a patient coupling end;
 an inspiratory connector end;
 an expiratory connector end; and
 a body extending between the patient coupling end, the inspiratory connector end, and the expiratory connector end, the body comprising:
  a patient branch at the patient coupling end;
  an inspiratory branch terminating at the inspiratory connector end, wherein the inspiratory branch comprises an inspiratory flow lumen having an inspiratory flow lumen axis, the inspiratory connector end configured to connect to an inspiratory conduit of a breathing circuit;
  an expiratory branch terminating at the expiratory connector end, wherein the expiratory branch comprises an expiratory flow lumen having an expiratory flow lumen axis, the expiratory connector end configured to connect to an expiratory conduit of the breathing circuit, wherein the inspiratory flow lumen axis is different from the expiratory flow lumen axis; and
  a merge region being configured to connect the inspiratory flow lumen, the expiratory flow lumen, and the patient branch;
  a first access port disposed on the body; and
  a second access port disposed on a first end of the merge region opposite of a second end of the merge region, the second end of the merge region proximate to the patient branch, the first end of the merge region located between the inspiratory branch and the expiratory branch, wherein the second access port comprises an introduction port configured to introduce medication into the merge region.

2. The wye connector of claim 1, wherein the first access port is positioned between the inspiratory connector end and the patient coupling end.

3. The wye connector of claim 2, wherein the first access port is positioned along the inspiratory branch and in fluidic communication with the inspiratory flow lumen.

4. The wye connector of claim 1, wherein the merge region comprises an intermediate lumen separated from the inspiratory flow lumen and the expiratory flow lumen by a wall.

5. The wye connector of claim 4, wherein the second access port is in fluidic communication with the intermediate lumen.

6. The wye connector of claim 1, wherein the body further comprises a gradation adjacent the second access port.

7. The wye connector of claim 6, wherein the gradation comprises a teethed protrusion.

8. The wye connector of claim 1, further comprising a cap configured to cover the second access port when the second access port is not in use.

9. The wye connector of claim 1, wherein the introduction port does not protrude into the patient branch.

10. A single piece wye connector comprising:
 a patient coupling end;
 an inspiratory connector end;
 an expiratory connector end; and
 a body extending between the patient coupling end, the inspiratory connector end, and the expiratory connector end, the body comprising:
  an inspiratory branch terminating at the inspiratory connector end, wherein the inspiratory branch comprises an inspiratory flow lumen having an inspiratory flow lumen axis, the inspiratory connector end configured to connect to an inspiratory conduit of a breathing circuit;
  an expiratory branch terminating at the expiratory connector end, wherein the expiratory branch comprises an expiratory flow lumen having an expiratory flow lumen axis, the expiratory connector end configured to connect to an expiratory conduit of the breathing circuit;
  a merge region being configured to connect the inspiratory flow lumen, the expiratory flow lumen, and a patient branch, wherein the merge region comprises an intermediate lumen separated from the inspiratory flow lumen and the expiratory flow lumen by a wall; and
  first and second access ports disposed on the body, the second access port being disposed on a first end of the merge region opposite of a second end of the merge region, the second end of the merge region proximate to the patient branch, the first end of the merge region located between the inspiratory branch and the expiratory branch, wherein the second access port comprises an introduction port configured to introduce medication into the connector.

11. The wye connector of claim 10, wherein the first access port comprises a probe port configured to receive a sensor probe.

12. The wye connector of claim 10, wherein the first access port is positioned between the inspiratory connector end and the patient coupling end.

13. The wye connector of claim 12, wherein the first access port is positioned along the inspiratory branch.

14. The wye connector of claim 12, wherein the first access port is in fluidic communication with the inspiratory flow lumen.

15. The wye connector of claim 10, wherein the second access port disposed on the merge region and in fluidic communication with the intermediate lumen.

16. The wye connector of claim 10, wherein the body further comprises a gradation adjacent the second access port.

17. The wye connector of claim 16, wherein the gradation comprises a teethed protrusion.

18. The wye connector of claim 10, further comprising a cap configured to cover the second access port when the second access port is not in use.

19. A single piece wye connector comprising:
 a patient coupling end;
 an inspiratory connector end;
 an expiratory connector end; and
 a body extending between the patient coupling end, the inspiratory connector end, and the expiratory connector end, the body comprising:
  an inspiratory branch terminating at the inspiratory connector end, wherein the inspiratory branch comprises an inspiratory flow lumen having an inspiratory flow lumen axis;
  an expiratory branch terminating at the expiratory connector end, wherein the expiratory branch comprises an expiratory flow lumen having an expiratory flow lumen axis;
  a merge region, wherein the merge region is configured to connect the inspiratory flow lumen, the expiratory flow lumen, and a patient branch, wherein the merge region comprises an intermediate lumen separated from the inspiratory flow lumen and the expiratory flow lumen by a wall;

a probe port disposed on the inspiratory branch; and a medication introduction port disposed on a first end of the merge region opposite of a second end of the merge region, the second end of the merge region proximate to the patient branch, the first end of the merge region located between the inspiratory branch and the expiratory branch.

20. The wye connector of claim 19, wherein the probe port is in fluidic communication with the inspiratory flow lumen.

21. The wye connector of claim 19, wherein the introduction port is in fluidic communication with the intermediate lumen.

22. The wye connector of claim 20, wherein the body further comprises a gradation adjacent the introduction port.

23. The wye connector of claim 22, wherein the gradation comprises a teethed protrusion.

24. The wye connector of claim 19, further comprising a cap configured to cover the introduction port when the introduction port is not in use.

* * * * *